US011308101B2

(12) United States Patent
Leighton et al.

(10) Patent No.: US 11,308,101 B2
(45) Date of Patent: Apr. 19, 2022

(54) MULTI-RESOLUTION MODELING OF DISCRETE STOCHASTIC PROCESSES FOR COMPUTATIONALLY-EFFICIENT INFORMATION SEARCH AND RETRIEVAL

(71) Applicants: Bonnie Berger Leighton, Newtonville, MA (US); Maxwell Aaron Sherman, Marblehead, MA (US); Adam Uri Yaari, Cambridge, MA (US)

(72) Inventors: Bonnie Berger Leighton, Newtonville, MA (US); Maxwell Aaron Sherman, Marblehead, MA (US); Adam Uri Yaari, Cambridge, MA (US)

( * ) Notice: Subject to any disclaimer, the term of this patent is extended or adjusted under 35 U.S.C. 154(b) by 0 days.

(21) Appl. No.: 17/459,346

(22) Filed: Aug. 27, 2021

(65) Prior Publication Data
US 2022/0092065 A1 Mar. 24, 2022

Related U.S. Application Data

(60) Provisional application No. 63/080,694, filed on Sep. 19, 2020.

(51) Int. Cl.
*G06F 16/2458* (2019.01)
*G06N 3/08* (2006.01)
(Continued)

(52) U.S. Cl.
CPC .......... *G06F 16/2462* (2019.01); *G06N 3/08* (2013.01); *G16B 5/20* (2019.02); *G16B 20/20* (2019.02); *G16B 40/00* (2019.02)

(58) Field of Classification Search
CPC ........ G06F 16/2462; G06N 3/08; G16B 5/20; G16B 20/20; G16B 40/00; G16B 99/00; G16B 20/00; G16B 5/00
See application file for complete search history.

(56) References Cited

U.S. PATENT DOCUMENTS

2014/0359422 A1\* 12/2014 Bassett, Jr ............. G16B 20/40
715/230
2017/0017749 A1\* 1/2017 Carmeli ................. G16B 20/00
(Continued)

FOREIGN PATENT DOCUMENTS

WO WO-2019084559 A1 \* 5/2019 ............. G16B 20/20

OTHER PUBLICATIONS

Lochovsky, Lucas, et al. "LARVA: an integrative framework for large-scale analysis of recurrent variants in noncoding annotations." Nucleic acids research 43.17 (2015): 8123-8134. (Year: 2015).\*
(Continued)

*Primary Examiner* — Jesse P Frumkin
(74) *Attorney, Agent, or Firm* — David H. Judson

(57) ABSTRACT

An activity of interest is modeled by a non-stationary discrete stochastic process, such as a pattern of mutations across a cancer genome. Initially, input genomic data is used to train a model to predict rate parameters and their associated uncertainty estimation for each of a set of process regions. For any arbitrary set of indexed positions of the stochastic process that are identified in an information query, the rate parameters and their associated estimation uncertainties are scaled using the model to obtain a distribution of the events of interest and their associated estimation uncertainties for the set of indexed positions. In one practical application, and in response to a search query associated with one or more base-pairs, a result is then returned. The result, which represents deviations between the estimated and observed mutation rates, is used to identify genomic elements that have more mutations than expected and therefore constitute previously unknown driver mutations.

16 Claims, 7 Drawing Sheets

(51) Int. Cl.
*G16B 20/20* (2019.01)
*G16B 40/00* (2019.01)
*G16B 5/20* (2019.01)

(56) References Cited

U.S. PATENT DOCUMENTS

2018/0365372 A1* 12/2018 Araya .................. G16B 5/00
2021/0222248 A1* 7/2021 Fu ....................... G16B 20/20

OTHER PUBLICATIONS

Martincorena, Iñigo, and Peter J. Campbell. "Somatic mutation in cancer and normal cells." Science 349.6255 (2015): 1483-1489. (Year: 2015).*

Nik-Zainal, Serena, et al. "Landscape of somatic mutations in 560 breast cancer whole-genome sequences." Nature 534.7605 ( 2016): 47-54. (Year: 2016).*

Juul, Malene, et al. "Non-coding cancer driver candidates identified with a sample-and position-specific model of the somatic mutation rate." Elife 6 (2017): e21778 (Year: 2017).*

Guo, Dandan, et al. "Deep Poisson gamma dynamical systems." arXiv preprint arXiv: 1810.11209 (2018). (Year: 2018).*

Schein, Aaron, et al. "Poisson-randomized gamma dynamical systems." Advances in Neural Information Processing Systems 32 ( 2019): 782-793. (Year: 2019).*

Juul, Malene, et al. "ncdDetect2: improved models of the site-specific mutation rate in cancer and driver detection with robust significance evaluation." Bioinformatics 35.2 (2019): 189-199. (Year: 2019).*

Mazarura, Jocelyn, Alta De Waal, and Pieter de Villiers. "A gamma-poisson mixture topic model for short text." Mathematical Problems in Engineering 2020 (2020). (Year: 2020).*

Lawrence, et al., "Mutational heterogeneity in cancer and the search for new cancer-associated genes," Nature 499, 214-218 (2013).

Polak, et al., "Cell-of-origin chromatin organization shapes the mutational landscape of cancer," Nature 518, 360-364 (2015).

* cited by examiner

MULTI-RESOLUTION MODELING OF DISCRETE STOCHASTIC PROCESSES FOR COMPUTATIONALLY-EFFICIENT INFORMATION SEARCH AND RETRIEVAL

BACKGROUND

Technical Field

This application relates generally to information search and retrieval wherein the activity of interest is described by a non-stationary discrete stochastic process (e.g., background mutation rate in the genome of a human malignant tumor).

Brief Description of the Related Art

Numerous natural domains involve modeling highly non-stationary discrete stochastic processes where the activity of individual units and groups of units vary dramatically over time and space. Such tasks include inferring neuronal activity from recorded brain signals, and modeling disease cases over the course of an outbreak. Since the underlying probabilistic principles are often unknown, data-driven strategies are required to uncover relevant properties. Machine learning in general and deep learning in particular have recently enabled such prediction within these complex non-linear stochastic spaces.

Numerous methods exist for modeling stationary stochastic processes. Far fewer exist for non-stationary processes because they are difficult to capture with the covariance functions of parametric models. Non-stationary kernels have been introduced for Gaussian processes, but these may not be tractable on large datasets due to computational complexity limitations. More recently, there has been work on developing Poisson-gamma models for dynamical systems, but these methods have focused on learning relationships between count variables, and not on predicting counts based on continuous covariates.

Tumors often contain many thousands of acquired mutations. A driver mutation is an alteration that gives a tumor cell a growth advantage for its neoplastic transformation; driver mutations differ from background (passenger) mutations, which, because they do not determine the development of the cancer, typically are harmless.

In the particular case of modeling mutation patterns across the cancer genome, numerous computational methods exist to model mutation rates within well-understood genomic contexts such as genes. These modeled regions account for <4% of the genome, and they are not applicable to most non-coding regions, where the majority of mutations occur. A handful of methods to model genome-wide mutation rates have been introduced, but they operate on a single length-scale or set of regions and require computationally-expensive retraining to predict over each new length-scale. Several other methods rely on Poisson or binomial regression; however, previous work has extensively documented that mutation counts data are over-dispersed, leading these models to underestimate variance and yield numerous false-positive driver predictions. Negative binomial regression has recently been used to account over-dispersion and perform genome-wide mutation modeling and driver detection, however, resolution was coarse and the approach only found a few, highly-recurrent driver mutations. Existing methods are also computationally slow.

In this domain, there remains a need to provide new methods and techniques to detect cancer-causing mutations to identify promising targets for diagnostic screening (e.g., using gene sequencing panels), and to facilitate drug research and development, as well as treatments.

BRIEF SUMMARY

Because cancer drivers reoccur across tumors, driver elements (genes, regulatory structures, and individual base-pairs) contain an excess of mutations in relation to that of the expected background mutations, which accumulate according to a non-stationary discrete stochastic process. According to this disclosure, a simple, efficient and accurate method to search for this recurrence is implemented using a probability distribution, which is referred to herein as a "Split Poisson-Gamma" (SPG) distribution, to model the discrete stochastic process at multiple resolutions, i.e., at any arbitrary length scale and without retraining. In a representative domain, namely, identifying causes of cancer, the framework is applied to capture cancer-specific mutation rates with high accuracy, resolution and efficiency, and in particular to identify candidate driver events that are then targeted for screening, therapeutic development, and treatment.

More generally, the technique herein provides for computationally-efficient information search and retrieval wherein an activity of interest is modeled as a non-stationary discrete stochastic process. To this end, the techniques herein provide a method of computationally-efficient information search and retrieval with respect to a probabilistic framework to model the distribution of a non-stationary discrete stochastic process at multiple length scales. Events of interest are assumed to occur within the stochastic process approximately independently at units i within a region R, and with an unknown rate $\lambda_R$ that is approximately constant across R, wherein $\lambda_R$ has an associated estimation uncertainty defined by a set of parameters that include expectation $\mu_R$ and variance $\sigma_R^2$. According to the method, a set of input data having a first dimensionality is used to train the model to predict rate parameters and their associated estimation uncertainty for each region R. Preferably, the model is trained by processing the input data through a first process (e.g., a Convolutional Neural Network (CNN)) that maps patterns in the input data to a reduced data set having a second dimensionality that is at least an order of magnitude less than the first dimensionality; thereafter (or concurrently with the CNN training), the reduced set is processed through a second process (e.g., a Gaussian Process (GP)) to output a distribution rate parameters and their associated estimation uncertainty for each region R. Then, and for any arbitrary set of indexed positions of the stochastic process of interest that are identified in an information query, and using a function computed in constant time, the rate parameters and their associated estimation uncertainties from the trained model are then scaled using the SPG to obtain a distribution of the events of interest and their associated estimation uncertainties for the set of indexed positions. The distribution is returned as a response to the information query. In a preferred embodiment, the function computed in constant time represents a closed form solution to a marginalization of a multi-variate probability distribution for the indexed positions. Advantageously, the information query and retrieval (including the scaling) is computationally-efficient and carried out without having to retrain the model.

In a representative practical application, the non-stationary discrete stochastic process represents a pattern of mutations across a cancer genome, and the events of interest are cancer-specific driver mutations. In response to a search query associated with one or more base-pair(s) (the arbitrary indexed position of interest), a result is then returned. The result, which represents deviations between the estimated and observed mutation rates, is used to identify genomic elements that have more mutations than expected and therefore constitute (perhaps previously unknown) driver mutations. Driver mutations identified using the modeling techniques herein are then targeted for diagnostic screening, early disease detection, disease progression detection, drug research and development, and other practical applications.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of how non-stationary stochastic process modeling predicts mutation patterns and identifies cancer-specific driver mutations, reference is now made to the following descriptions taken in conjunction with the accompanying drawings, in which.

DETAILED DESCRIPTION

The subject matter herein integrates a deep learning framework with a probabilistic model to learn a discrete stochastic process at arbitrary length scales for generalized information search and retrieval, e.g., to accurately and efficiently model mutations load in a tumor and detect cancer driver mutations genome-wide. The probability model has a closed-form posterior, enabling efficient and accurate linear-time prediction over any length scale after the parameters of the model have been inferred a single time. In the following description, the framework is described in a particular domain (i.e. model mutation rates in tumors and show that model parameters can be accurately inferred from high-dimensional epigenetic data) using a convolutional neural network, a Gaussian process, and maximum-likelihood estimation, but the methodology is broadly applicable to other domains, as the technique is both more accurate and more efficient than existing models over a large range of length scales (or, more generally, any arbitrary set of indexed positions of the stochastic process). Thus, and as will be seen, the approach demonstrates usefulness of multi-resolution modeling by detecting events of interest over any length-scale of a discrete stochastic process.

FIGS. 1A-1E depict the techniques of this disclosure wherein non-stationary stochastic process modeling is used to predict mutation patterns and identify cancer-specific driver mutations. This application is not intended to be limiting, as the approach herein may be generalized to provide anomaly detection with respect to other application domains wherein events of interest are described by a non-stationary stochastic process. In this type of process, the relevant events of interest occur (within the process) approximately independently at units i within a region R, and at an unknown rate $\lambda_R$ that is approximately constant, wherein $\lambda_R$ has an associated estimation uncertainty defined by a set of parameters that include expectation $\mu_R$ and variance $\sigma_R^2$.

Figure 1A:
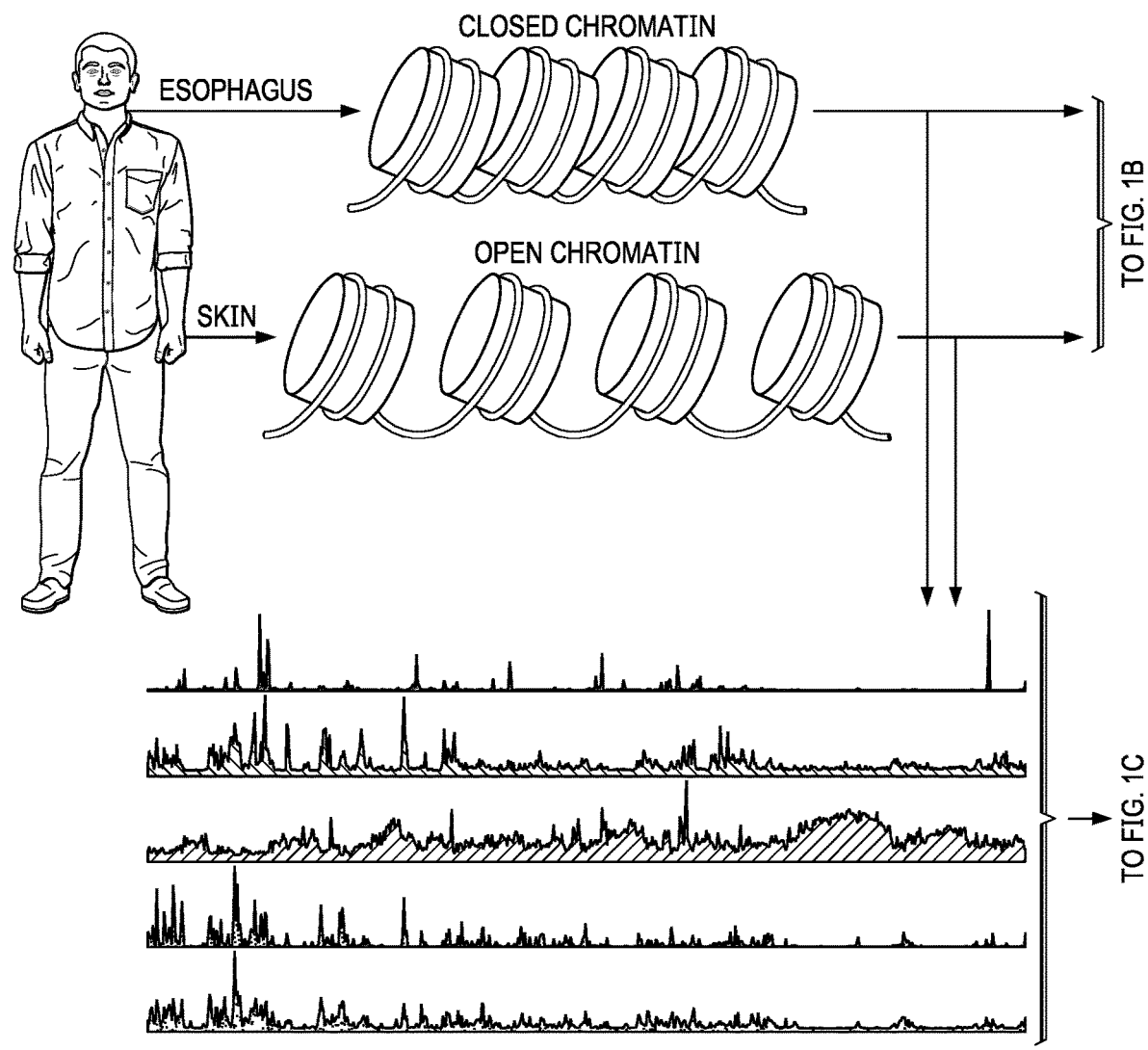
FIG. 1A depicts areas of a genome having varying epigenetic states (e.g., accessibility for transcription depending on tissue type.
Figure 1B:
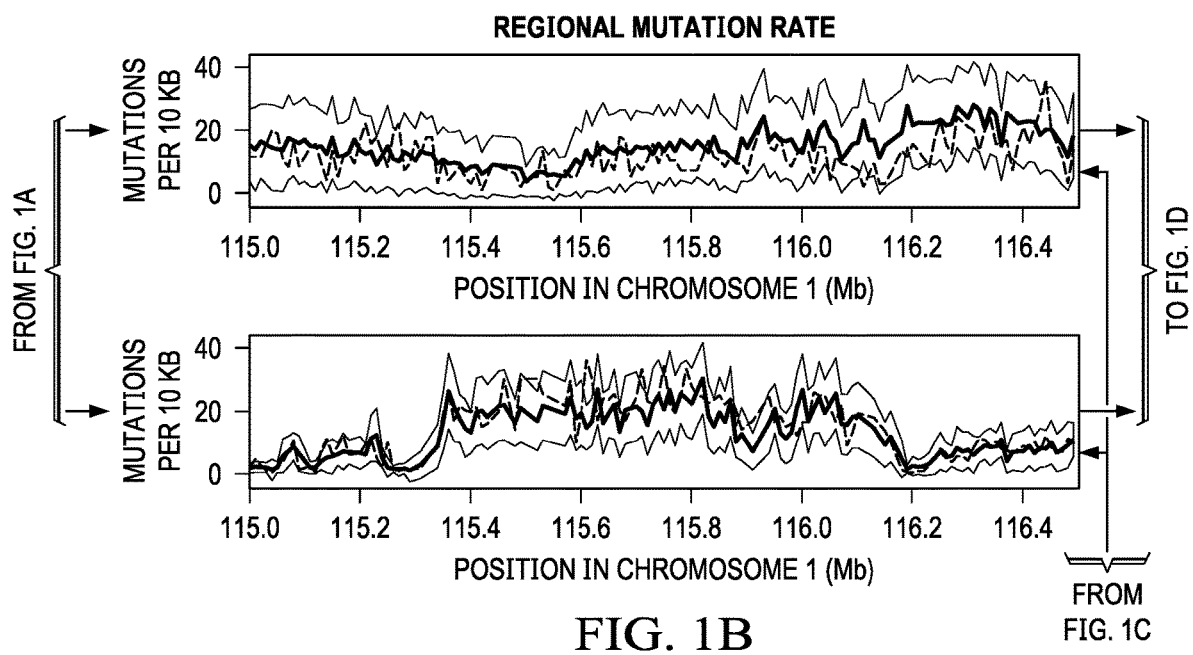
FIG. 1B depicts these epigenetic states have different mutation rates in different tissues.
Figure 1C:
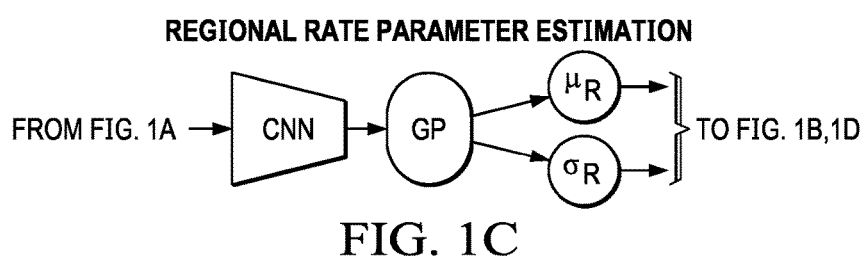
FIG. 1C depicts how a model according to this disclosure takes these epigenetic tracks as input to estimate regional mutation density across the genome (e.g., with a 95% confidence interval)
Figure 1D:
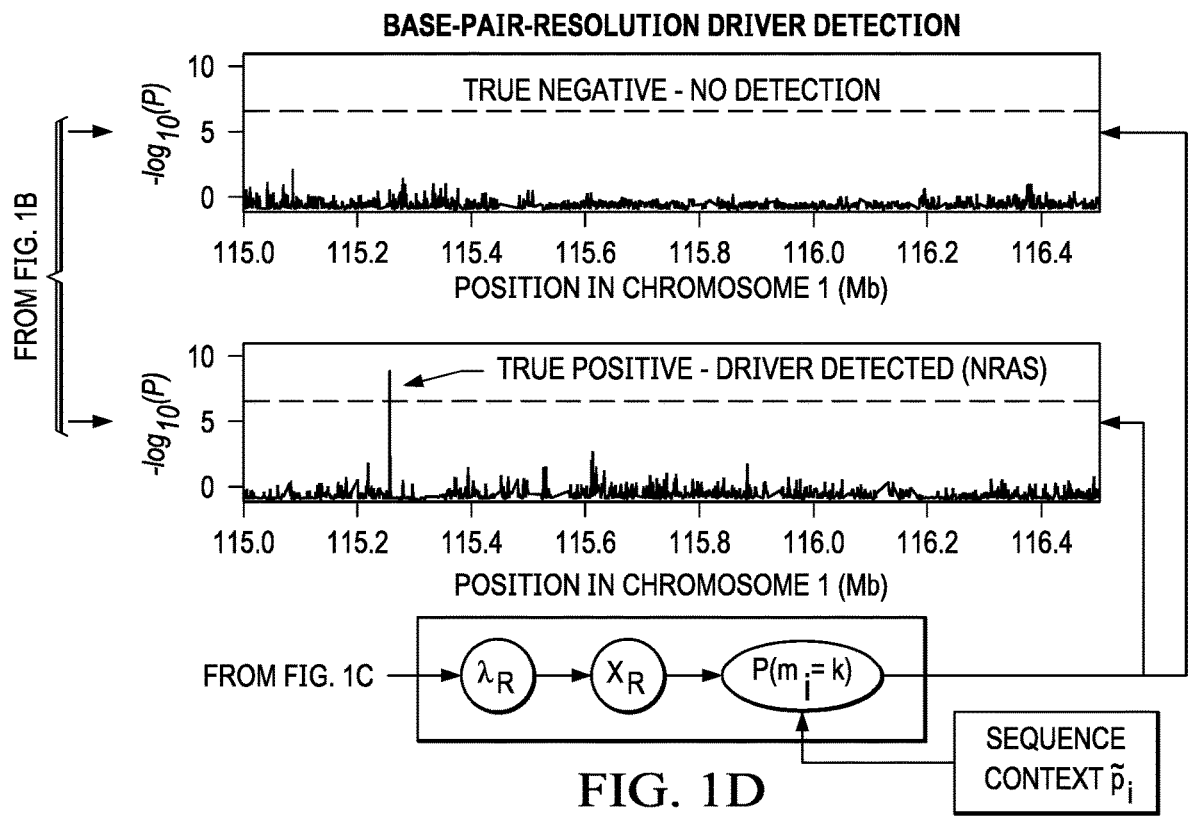
FIG. 1D depicts the regional rate parameters and sequence context are then integrated in a closed form Graphical Model (GM) for the Split-Poisson-Gamma (SPG) distribution to provide arbitrary resolution mutation count estimates for any arbitrary indexed set of positions (e.g., some scale length) of the process, wherein deviations between the estimated and observed mutation rates identify mutations that are associated with cancers in different tissues.
Figure 1E:
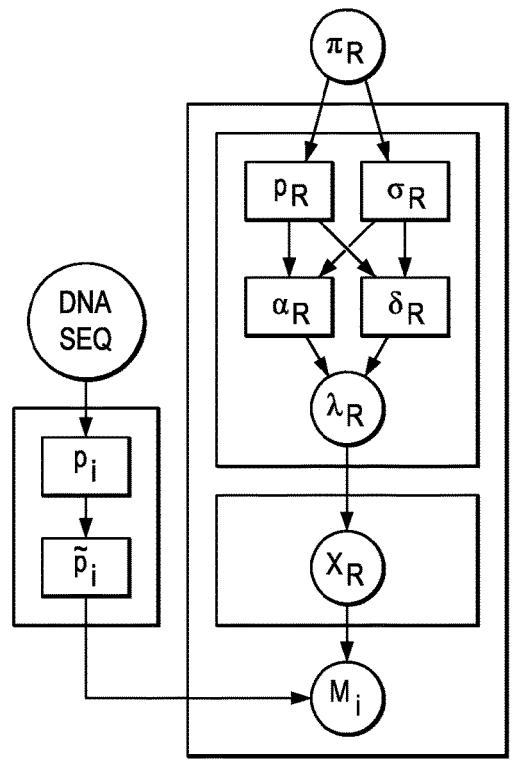
FIG. 1E is a plate diagram depicting the Split-Poisson-Gamma (SPG) model.

FIG. 1A depicts areas of a genome having varying epigenetic states (e.g., accessibility for transcription depending on tissue type. FIG. 1B depicts that these epigenetic states associate with different mutation rates in different tissues. As will be described in more detail below, FIG. 1C depicts how a model according to this disclosure takes these epigenetic tracks as input to estimate regional mutation density across the genome (e.g., with a 95% confidence interval). FIG. 1D depicts how the regional rate parameters and a sequence context are then integrated in a closed form Graphical Model (GM) via a Split-Poisson-Gamma (SPG) distribution to provide arbitrary resolution mutation count estimates for any scale length of the process, wherein deviations between the estimated and observed mutation rates identify mutations that are likely to drive cancers in different tissues. FIG. 1E is a plate diagram depicting the SPG model, wherein squares depict inferred parameters.

Figure 2A:
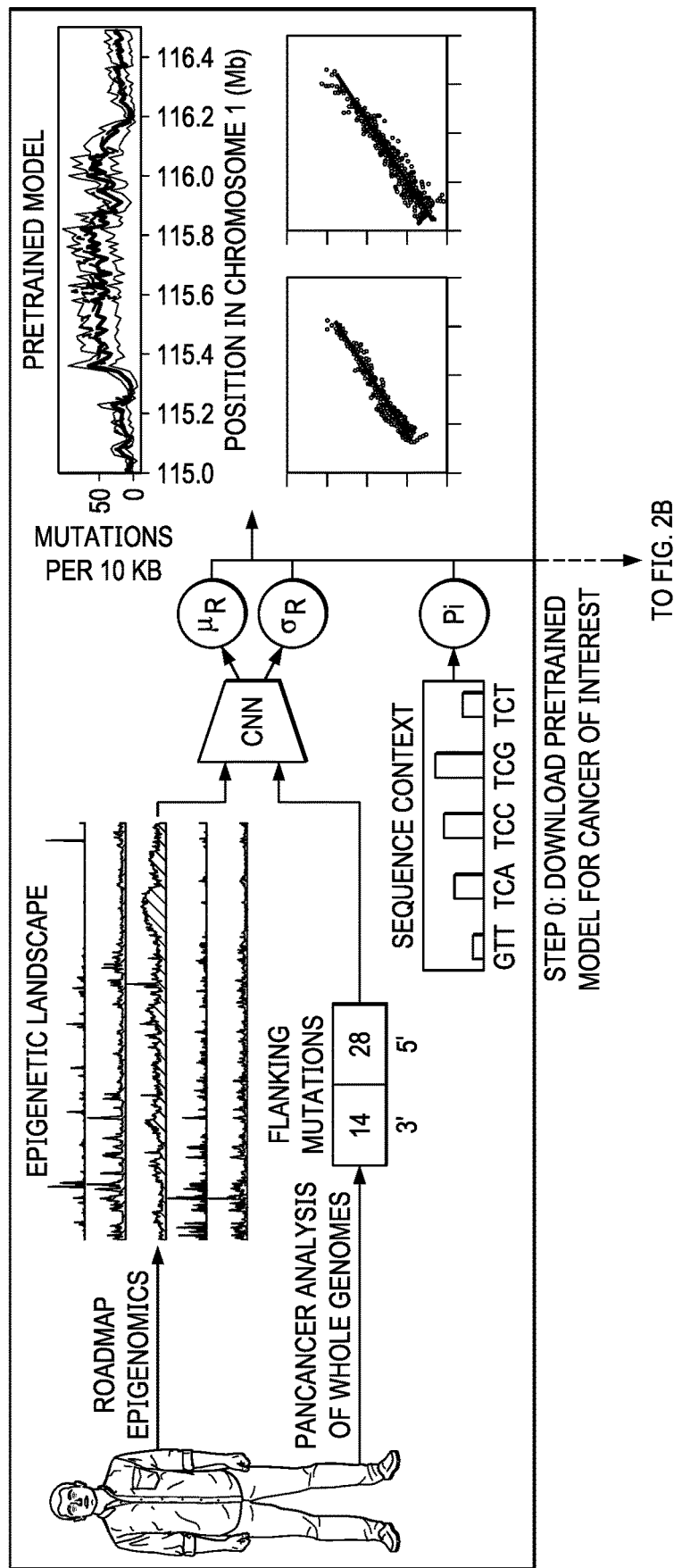
FIG. 2 is a detailed process flow of the information search and retrieval technique of this disclosure.
Figure 2B:
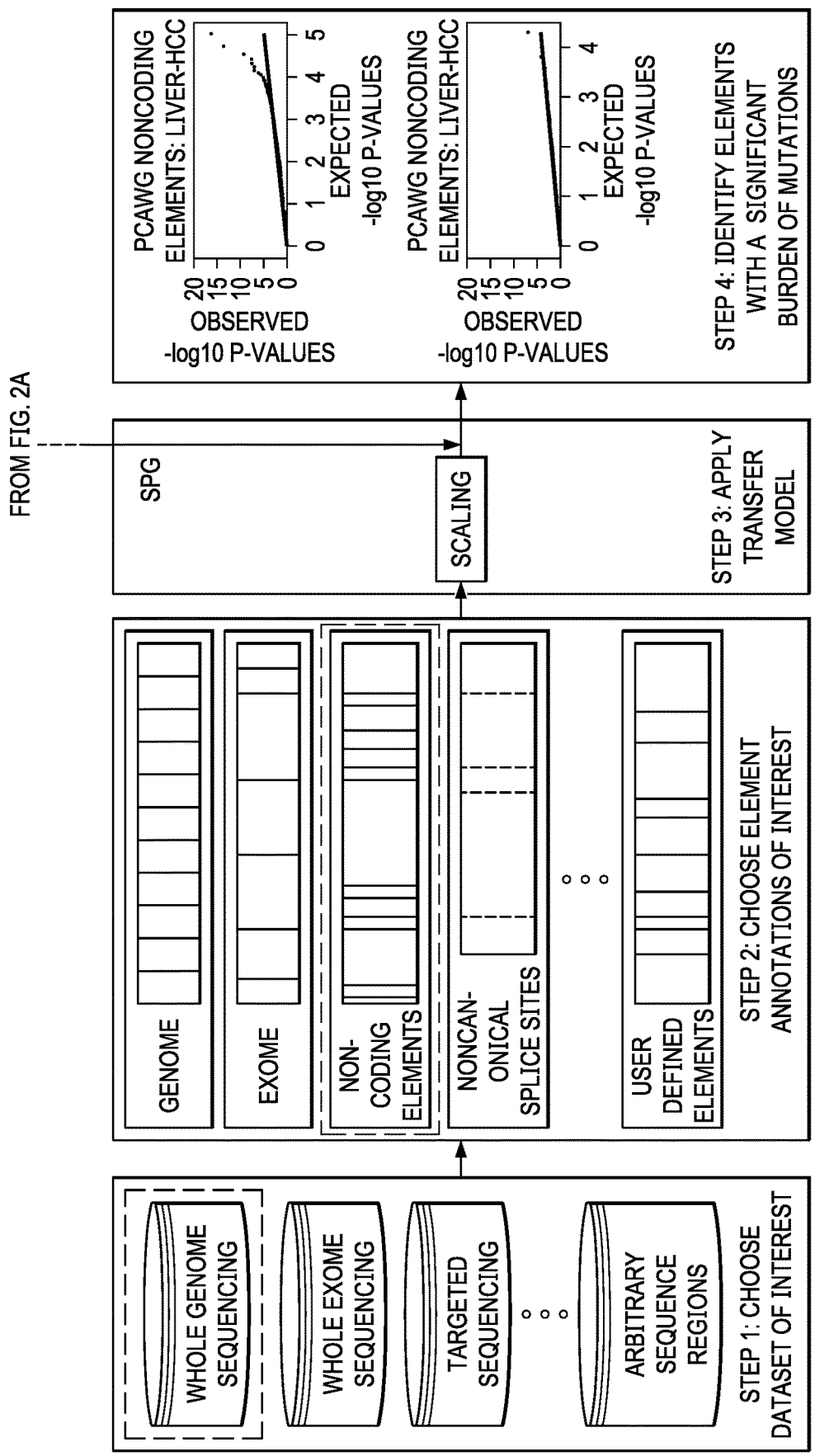

FIG. 2 depicts at a high level a method of information search and retrieval for anomaly detection associated with a non-stationary discrete stochastic process according to this disclosure. As noted above, events of interest occur within the process approximately independently at units i within a region R, and at an unknown rate $\lambda_R$ that is approximately constant, wherein $\lambda_R$ has an associated estimation uncertainty defined by a set of parameters that include expectation $\mu_R$ and variance $\sigma_R^2$. The top portion of the figure details the creation of the pretrained model for the particular cancer of interest. As previously described, in this process a set of input data having a first dimensionality is received. The model is trained to predict rate parameters and their associated estimation uncertainty for each region R. To this end, preferably the input data is first applied to a Convolutional Neural Network (CNN) that maps patterns in the input data to a reduced data set having a second dimensionality that is at least an order of magnitude less than the first dimensionality. The reduced set is then processed through a Gaussian Process (GP) (not shown) to output a distribution of the events of interest and their associated estimation uncertainty for each region R. This training need only be carried out once. The remainder of the figure details how the pretrained model is then used. In particular, at Step 0 the pretrained model for the cancer of interest is downloaded. At Step 1, a dataset of interest is chosen from various techniques such as whole genome sequencing, whole exome sequencing, targeted sequencing, or some other identification of arbitrary sequence regions. Step 2 depicts user selection of element annotations of interest. At Step 3, and following application of the scaling function, the SPG model is applied. The scaling function is computed in constant time (and depends on the search query), and it operates to scale the rate parameters and their associated estimation from the trained model to obtain a distribution of the events of interest and their associated estimation uncertainties for any length scale of interest as specified in Step 2. In response, and as shown in Step 4, elements with a significant burden of mutations are identified.

Advantageously, the scaling function shown in FIG. 2 is computationally-efficient and carried out without having to retrain the model. These benefits derive from the Split-Poisson-Gamma (SPG) model, and (responsive to the search query) result in a distribution over the events of interest that is then used to enable a practical application, e.g., anomaly detection, early tumor detection, treatment guidance, and others.

The following further describes the discrete stochastic process modeling technique of this disclosure.

Multi-Resolution Modeling of a Non-Stationary Discrete Stochastic Process

Consider a non-stationary discrete stochastic process $\{M_i;\ i=1, 2, \ldots\}$ where $M_i$ is the integer-valued event count at position i. Associated with each position i is a real-valued, L-dimensional feature vector $\eta_i$ that determines the instantaneous event rate $\lambda_i$ via an unknown function. Thus, a region $R=\{i, i+1, \ldots, i+N\}$ of N contiguous positions is characterized by an L×N feature matrix $\eta_R$ and an event count $X_R = \Sigma_{i \in r} M_i$. As training data, $\eta_R$, $X_R$ and $M_i$ are observed for some set of regions $\{R \in \mathcal{T}\}$. Then, given a set of features matrices from unobserved regions $\{\eta_R; R \in \mathcal{H}\}$, the challenge is to predict the distribution of event counts over any arbitrary set I of unseen positions that may or may not be contiguous. Real-world examples include mutations accumulating at positions in the genome, packets delivered to routers in a network, traders in a stock market, and others.

The Split-Poisson-Gamma Process

Assume that the process is near-stationary within a small enough region $R=\{i, i+1, \ldots, i+N\}$ and that the L×N covariate matrix $\eta_R$ is observed. Thus, the rate of events $\lambda_R$ within R is approximately constant and associated with $\eta_R$, albeit in an unknown way. A number of events ($X_R$) may occur within R dependent on $\lambda_R$ and are then stochastically distributed to individual positions within R, implying a hierarchical factorization of the scalar random variables $\lambda_R$, $X_R$, and $M_i$ as:

$$Pr(M_i=k, X_R, \lambda_R; \eta_R) = Pr(M_i=k|X_R;\eta_R)Pr(X_R|\lambda_R;\eta_R)Pr(\lambda_R;\eta_R). \quad (1)$$

$X_R$ and $\lambda_R$ are unknown nuisance variables and are marginalized in general as:

$$Pr(M_i = k \mid \eta_R) = \quad (2)$$

$$\int_0^\infty Pr(\lambda_R; \eta_R) \sum_{X_R=k}^\infty Pr(M_i = k \mid X_R; \eta_R)\ Pr(X_R \mid \lambda_R; \eta_R) d\lambda_R.$$

Because applications often require many posterior predictions over regions of varying sizes, this disclosure proposes a prior parameterization that builds on the success and flexibility of a classical Poisson-Gamma distribution while ensuring the marginalization has an easy-to-compute posterior distribution:

$$\lambda_R \sim \text{Gamma}(\alpha_R, \theta_R) \quad (3)$$

$$X_R \sim \text{Poisson}(\lambda_R) \quad (4)$$

$$M_i \sim \text{Binomial}(X_R, \tilde{p}_i) \quad (5)$$

where $\alpha_R$ and $\theta_R$ are shape and scale parameters dependent on $\eta_R$, $p_i$ is the time-averaged probability of an event at i and $$\tilde{p}_i = \frac{p_i}{\sum_{j \in R} p_j},$$

the normalized probability within R. A plate diagram of the hierarchical model is depicted in FIG. 1(e).

The above formulation provides a simple, closed form solution to equation (2) as a negative binomial (NB) distribution (as also explained further below):

$$Pr(M_i = k \mid \alpha_R, \theta_R, \tilde{p}_i; \eta_R) = NB\left(k; \alpha_R, \frac{1}{1 + \theta_R \cdot \tilde{p}_i}\right) \quad (6)$$

Equation (5) implicitly assumes that events are distributed independently to units within R. Exploiting this assumption, equation (6) generalizes to consider any se of units $I \subseteq R$ as:

$$Pr\left(\sum_{i \in I} M_i = k \mid \alpha_R, \theta_R, \{\tilde{p}_i\}_{i \in I}; \eta_R\right) = NB\left(k; \alpha_R, \frac{1}{1 + \theta_R \cdot \sum_{i \in I} \tilde{p}_i}\right). \quad (7)$$

The above formulation is an extension of the classical Poisson-Gamma distribution whereby the Poisson is randomly split by a binomial. This is the Split-Poisson-Gamma (SPG) distribution as referenced above. While the derivation of the SPG solution makes simplifying assumptions, a significant benefit is that the parameters $\alpha_R$ and $\theta_R$ need to be estimated only once for each non-overlapping region R. If a new region R' is larger than R, the gamma distribution in a super-region containing R' is approximated as a superposition of the previously-inferred parameters of each region of size R within the super-region, as further explained below.

Inferring Regional Rate Parameters

The statistical power of SPG depends on accurate estimation of the regional gamma parameters $\alpha_R$ and $\theta_R$. Here, a variational approach is used to enable flexible, accurate, and non-linear inference of these parameters from a set of covariates. Let $G(\alpha, \theta)$ be a gamma distribution. By the central limit theorem $$\lim_{\alpha \to \infty} G(\alpha, \theta) = N(\mu, \sigma^2),$$

where $\mu=\alpha\theta$ and $\sigma^2=\alpha\theta^2$. Thus, a Gaussian process (GP) is used to non-linearly map covariates to regional estimates for $\mu_R$ and $\sigma_R^2$. The variational estimates for the gamma parameters are then:

$$\alpha_R = \mu_R^2/\sigma_R^2, \theta_R = \mu_R/\sigma_R^2 \tag{8}$$

For a super-region $R'=R_i+R_j$, $\mu_{R'}=\mu_{R_i}+\mu_{R_j}$ and $\sigma_{R'}^2+\sigma_{R_j}^2$.

A limitation of this approach is that GPs only operate on vectors of covariates. Thus, preferably a dimensionality reduction method is applied to the input matrix $\eta_R$. In cases where $\eta_R$ includes spatial relationships, preferably a convolutional neural network is used to implement dimension-reduction, however, this is not a limitation. Other approaches may be used, as discussed below.

Inferring Time-Averaged Event Probabilities

The time-averaged parameters $\{p_i; i=1,2,\ldots\}$ must also be inferred. As seen in equation (5), these parameters are not used directly; instead, they are renormalized to sum to one within a region of interest. Thus, estimates do not need to reflect the absolute probability of an event at i but merely the relative rate of events between positions. Because of the renormalization procedure, the estimates need not even be a true probability distribution. Thus clustering is dependent on the application of interest.

Methods

The following provides additional details regarding the methods described above.

SPG

The following describes how to derive the closed form negative binomial distribution presented above as the SPG marginal distribution over events at some unit i in a region R. To this end, the following notation is adopted:

$M_i$: # mutations observed at position i (observed);
$p_i$: genome-wide probability of observing a mutation at the nucleotide context of i (inferred);
$\tilde{p}_i$: normalized probability of observing a mutation at i in region R (inferred);
$\lambda_R$: the background mutation rate in region R (unobserved);
$X_R$: # background mutations in region R (unobserved);
$\mu_R$: the expected background mutation rate in region R (inferred);
$\sigma_R^2$: the variance of background mutation rate in region R (inferred); and
$\eta_R$: covariates associated with the behavior of the stochastic process within R (observed).

As described above and depicted in FIG. 1, the graphical model implies the factorization:

$$Pr(M_i, X_R, \lambda_R | \alpha_R, \theta_R, \tilde{p}_i; \eta_R) = Pr(M_i = k | X_R, \tilde{p}_i; \eta_R) \cdot Pr(X_R = x | \lambda_R; \eta_R) \cdot Pr(\lambda_R | \alpha_R, \theta_R; \eta_R) \tag{equation (10)}$$

where:

$$\alpha_R = \mu_R^2/\sigma_R^2$$

$$\theta_R = \sigma_R^2/\mu_R.$$

Because $\eta_r$ is a given in each equation, it is suppressed below for notational ease.

To marginalize out $X_R$, note that:

$$Pr(M_i = k | \lambda_R) = \sum_{x=k}^{\infty} Pr(M_i = k | X_R, \tilde{p}_i) \cdot Pr(X_R = x | \lambda_R),$$

which is equivalent to a split Poisson process. Thus:

$$Pr(M_i = k | \lambda_R) = \text{Poisson}(M_i = k; \tilde{p}_i \lambda_R). \tag{11}$$

Now, marginalize out the unknown rate parameter $\lambda_R$:

$$P(M_i = k | \tilde{p}_i, \alpha_R, \theta_R) = \int_0^\infty P(M_i = k | \lambda_R; \tilde{p}_i) P(\lambda_R | \alpha_R, \theta_R) d\lambda_R$$

$$= \int_0^\infty \frac{(\tilde{p}_i \lambda_R)^k}{k!} e^{-\tilde{p}_i \lambda_R} \frac{1}{\Gamma(\alpha_R)\theta_R^{\alpha_R}} \lambda_R^{\alpha_R - 1} e^{-\lambda_R/\theta_R} d\lambda_R$$

$$= \frac{\tilde{p}_i^k}{k!\Gamma(\alpha_R)\theta_R^{\alpha_R}} \int_0^\infty \lambda_R^{\alpha_R + k - 1} e^{-\lambda_R(\tilde{p}_i + 1/\theta_R)} d\lambda_R.$$

Now, making a substitution $t=\lambda(\tilde{p}_i+1/\theta_R)$, and noting that the resulting integrand is an un-normalized gamma distribution:

$$P(M_i = k | \tilde{p}_i, \alpha_R, \theta_R) = \frac{\tilde{p}_i^k}{k!\Gamma(\alpha_R)\theta_R^{\alpha_R}} \Gamma(\alpha_R + k) \left(\frac{1}{\tilde{p}_i + 1/\theta_R}\right)^{\alpha_R + k}$$

$$= \frac{\Gamma(\alpha_R + k)}{k!\Gamma(\alpha_R)} \left(\frac{\tilde{p}_i \theta_R}{\tilde{p}_i \theta_R + 1}\right)^k \left(\frac{1}{\tilde{p}_i \theta_R + 1}\right)^{\alpha_R}$$

$$= NB\left(M_i = k; \alpha_R, \frac{1}{\tilde{p}_i \theta_R + 1}\right).$$

Parameter Estimation Procedure

The training data comprises a set of matrices $\{\eta_R; R \in \mathcal{T}\}$ and associated mutation counts $\{X_R; R \in \mathcal{T}\}$. In one embodiment, a convolutional neural network (CNN) is trained to take $\eta_R$ as input and predict $X_R$ as output, e.g., using mean squared error loss. The final (e.g., 16-dimension) vector of the trained CNN is then used as input to train a Gaussian process to predict the mutation count $X_R$ and the associated estimation uncertainty, e.g., by maximizing the likelihood of the observed data. In this embodiment, the mean and variance output by the GP are used as estimates for $\mu_R$ and $\sigma_R^2$.

In the case of cancer mutation patterns, it has been shown that the mutation rate at any position i is heavily influenced by the nucleotide at i and the two nucleotides directly adjacent to i; positions with this same trinucleotide context will have similar mutation patterns. This trinucleotide context is used to estimate $p_i$. (The 3 mer genomic context is an arbitrary modeling choice here, and any other model that provides genomic base-pair resolution probability may be used). In particular, let n, t, n' be the trinucleotide context centered at position i. The time-average probability of an event at $p_i$ may be estimated based on its trinucleotide composition n, t, n', where n is the nucleotide at i−1, t is the nucleotide at i and n' is the nucleotide at i+1 in the reference genome. In an exemplary embodiment, every occurrence of n, t, n' in the human genome is first counted; then, the number of times the middle nucleotide of the 3 mer was mutated across the genome is counted. The maximum likelihood estimate of $p_i$ is then the ratio of the number of observed mutations of the 3 mer divided by the total occurrences of the 3 mer.

Data

As is well-known, high-throughput genome sequencing works by randomly reading millions of short sequences of nucleotides (36-150 bases in length) from a target genome. These "reads" are then mapped to the human reference genome to reconstruct a target.

Because input data sets are large, preferably significant dimension reduction is implemented before the GP-based variational strategy is employed to infer SPG regional rate parameters. In a preferred embodiment, a CNN is used to produce a low-dimensional embedding that retrains information about structures of interest in the input data (e.g., local epigenetic patterns). Generalizing, the supervised nature of a CNN further enables the resulting embedding to be optimized for the cancer of interest, which is crucial to performance because epigenetic determinants of mutation rate vary drastically between cancer types.

In one experiment, the model is first trained, e.g., using an artificial dataset with known mean and variance parameters dependent on an observed input matrix. These artificial datasets are created using input matrices of size 735×100, from epigenetic tracks for non-overlapping regions of 50,000 positions. To this end, 733–$\log_{10}$ (P-value) chromatin tracks representing the epigenetic organization of 111 human tissues were obtained from Roadmap Epigenomics Consortium. These tracks measure the abundance of a particular chromatin mark genome-wide, with smaller (more significant) p-values reflecting a greater abundance of the chromatin mark at a genomic position. Chromatin marks are chemical modifications of histones, the proteins used to package DNA within a cell. Additionally, ten replication timing tracks were obtained from the ENCODE consortium. Replication timing assays measure the relative time at which position in the genome is replicated during cell division. For non-overlapping regions R of predefined size and location, average nucleotide content is calculated, and the mean values for each region is calculated as the mean chromatin signal for each track in the region. Publicly-available mutation count data (ICGC subset of the Pan-Cancer Analysis of Whole Genomes Consortium) were obtained for certain cancers, and somatic single-base substitution mutations were summarized as mutation counts per window for various window sizes of 50 bp, 100 bp, 500 bp, 1 kb, 5 kb, 10 kb, 25 kb, 50 kb, 100 kb, and 1 Mb.

To define non-stationary mean and variance of mutation rate dependent on each region's input matrix, $\eta_R$ is reduced to a feature vector of size 735 by taking the mean across columns, and using a k-nearest neighbors (KNN) strategy to identify 500 regions with similar epigenetic feature vectors; the mean $\mu_R$ and variance $\sigma_R^2$ are defined for each region as the mean and variance of the observed event counts across its 500 neighboring regions. The number of observed events for that region was then randomly drawn from a binomial distributions defined by those parameters. Models were trained on the randomly drawn counts and evaluated on their ability to accurately infer the true mean and variance.

Gaussian Process Feature Vector Generation (Dimension Reduction)

In one example implementation, the input matrices $\eta_R \in \mathbb{R}^{735 \times 100}$ are sufficiently large so as to require significant dimension reduction before the GP-based variational strategy is employed to infer SPG regional rate parameters. (The example sizing here is not intended to be limiting, as the size of the input data set will vary depending on implementation; in certain circumstances the input data may not require dimension reduction). Columns encode the high-resolution spatial organization of the epigenome which have been shown to be important determinants of local mutation rate. Thus, in an example embodiment, the CNN used for dimension reduction contains four (4) convolutional blocks with two (2 batch normalized convolutional layers and ReLU activation. The first block transformed the input tensor from 735×100 to 256×50 with 256 channels and a double stride. The other blocks are ResNet-style residual blocks that maintain their input dimension to facilitate residual connections, with 256, 512 and 1024 channels respectively. Between each of the three (3) residual blocks there is a double stride (ReLU activated and batch normalized) convolutional layer, which divides the tensor length by two and doubles its height with additional channels. The output of the last residual block is flattened and passed through three (3) fully-connected layers. The first two are ReLU activated and reduce the dimensionality of the tensor to 128 and 16 dimensions respectively. The last uses linear functions to reduce the tensor to a single cell holding the output of the regression. This forces a linear relation between the regression output and the last feature layer, thus simplifying the function the GP needs to learn, thereby improving GP accuracy.

Alternative embodiments to the CNN include a Fully-Connected Neural Network (FCNN). The FCNN has an architecture similar to the CNN's 3 fully-connected layers but with an input space of the mean epigenetic vector (735 dimensions). Thus, the FCNN is computationally similar to the CNN but operates on the mean vector instead of the full matrix as an input. Another alternative to providing dimension reduction is an Auto-Encoder Neural Network (AE), which has two identical but opposite networks (an encoder, and a decoder) co-training; both encoder and decoder have the same architecture as the CNN, but the decoder network is upside down, propagating the condensed information from the encoder to the original input dimension. Still other dimensionality-reduction methods include Principal Component Analysis (PCA) and Uniform Manifold Approximation and Projection (UMAP).

Gaussian Process and Alternatives

In the example embodiment, a sparse, inducing-point Gaussian process (Titsias) with a radial basis function kernel was implemented using Python's GPyTorch package. The GP was optimized with 2000 inducing points using the Adam optimizer for 100 steps. All features were mean-centered and standardized to unit variance prior to training. For each dataset, the GP was run ten independent times and the ensemble mean of the mean and variance predictions from each of the individual runs calculated. The ensemble predictions were then used as the mean and variance for each region.

Alternative models for the estimation of $\mu_r$ and $\sigma_R^2$ (i.e., without the use of GP) use the mean epigenetic vector as an input. These include Random Forest (RF), Negative Binomial Regression (NBR), and Binomial Regression (BR).

Figure 3A:
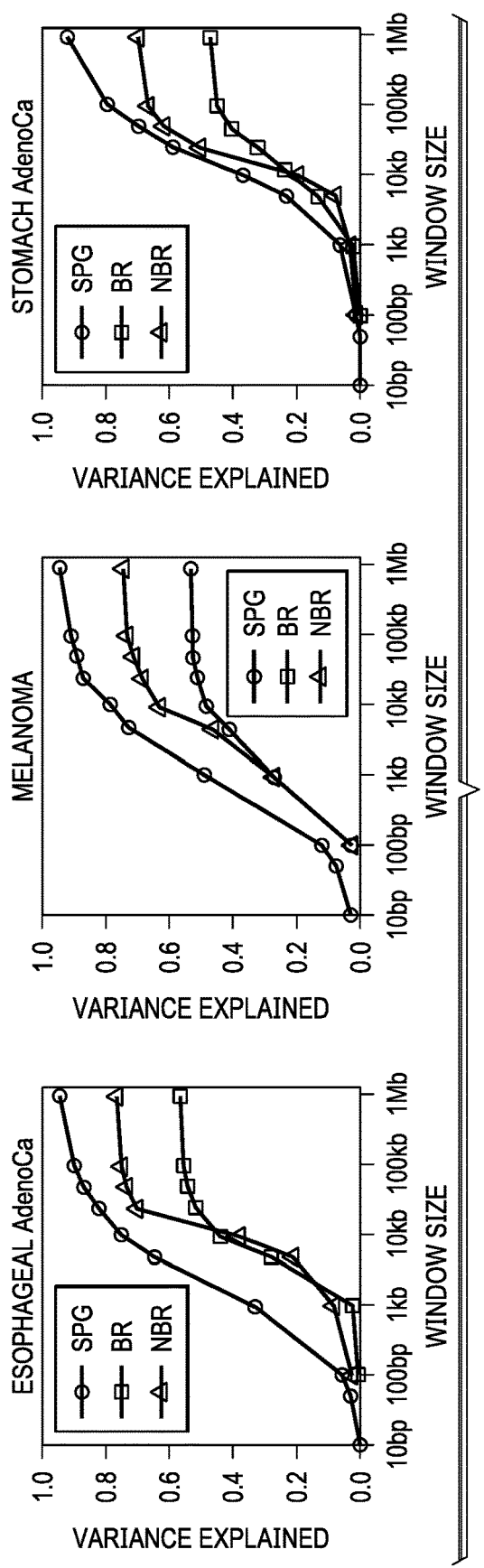
FIG. 3A depicts variance explained (Pearson $R^2$) of the observed mutation count by SPG versus binomial regression (BR) and negative binomial regression (NBR) across length-scales for three different cancers, namely, esophageal adenocarcinoma, melanoma and stomach adenocarcinoma)
Figure 3B:
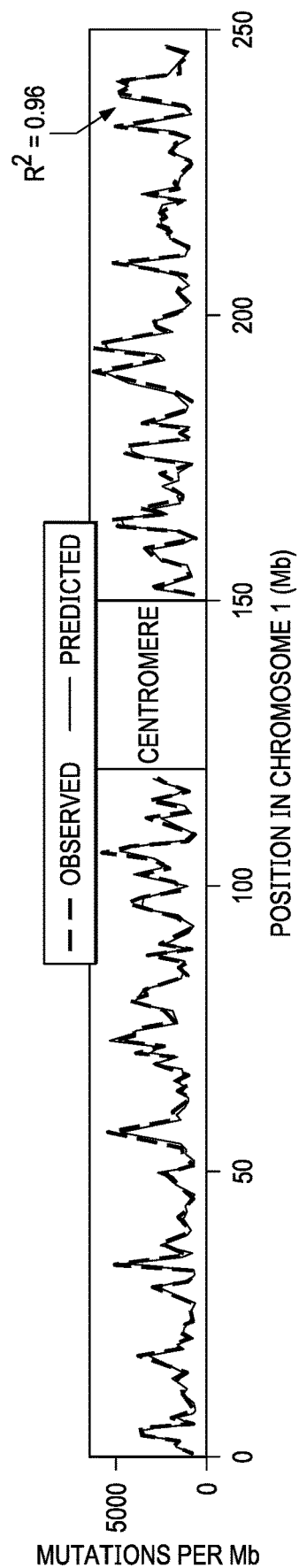
FIG. 3B depicts observed (dashed) and predicted (solid) mutation density from the GM at 1 Mb regions across chromosome 1 in melanoma.
Figure 3C:
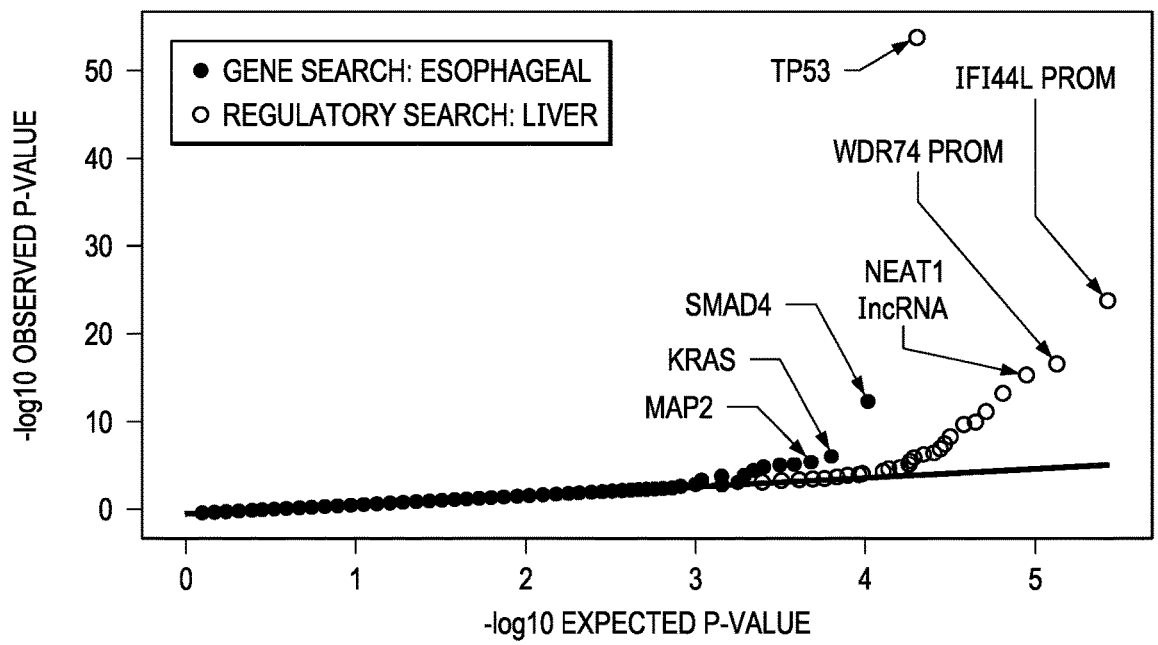
FIG. 3C depicts quantile-quantile plots of expected and observed P-values for gene driver detection in esophageal adenocarcinoma and driver regulatory element detection in liver cancer.
Figure 3D:
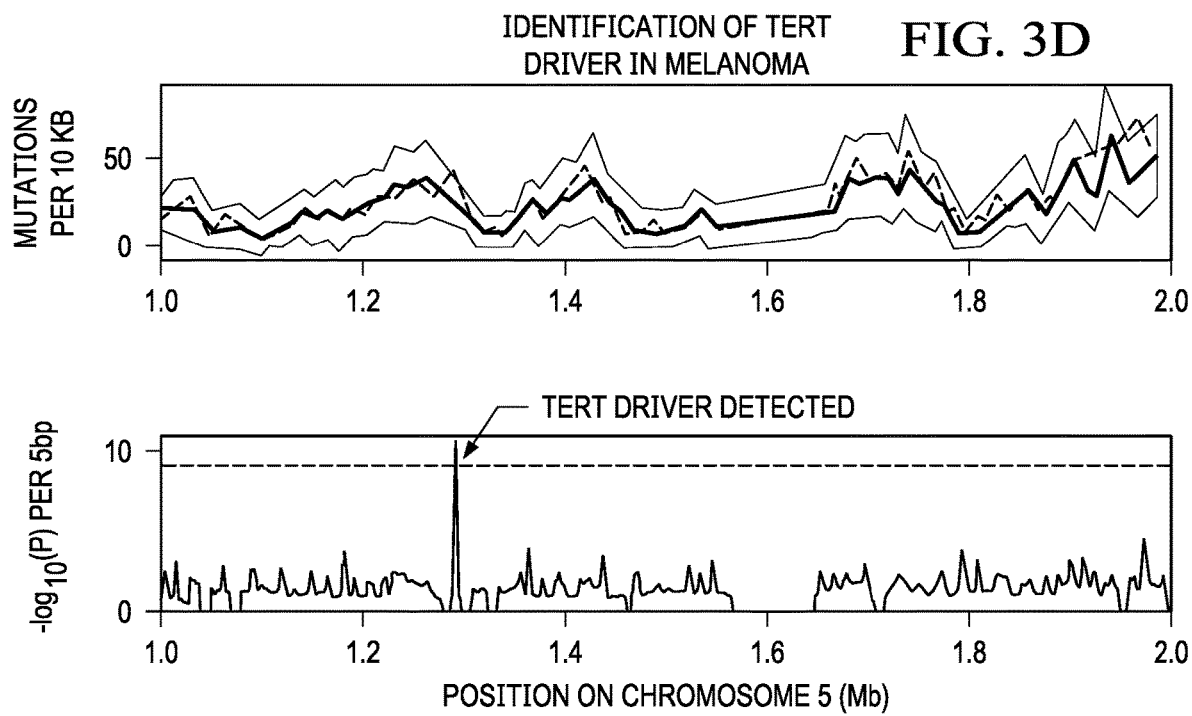
FIG. 3D depicts model detection of a well-known non-coding driver in the TERT promotor in melanoma at 1 kb resolution.

SPG accurately models mutation density and detects driver events. In particular, FIG. 3A depicts variance explained (Pearson $R^2$) of the observed mutation count by SBP versus binomial regression (BR) and negative binomial regression (NBR) across length-scales for three different cancers, namely, esophageal adenocarcinoma, melanoma and stomach adenocarcinoma). FIG. 3B depicts observed (dashed) and predicted (solid) mutation density from the SPG at 1 Mb regions across chromosome 1 in melanoma. FIG. 3C depicts quantile-quantile plots of expected and observed P-values for gene driver detection in esophageal adenocarcinoma and driver regulatory element detection in liver cancer. FIG. 3D depicts model detection of a well-known non-coding driver in the TERT promotor in melanoma at 1 kb resolution.

SPG differs from NBR in several important respects that help explain its improved performance: (1) SPG models mutation patterns over arbitrary sets of positions enabling it to dynamically pool information across positions after a single training; in contrast, NBR operates on fixed regions and must be retrained for every new region size; (2) SPG's variational inferencing estimates the gamma parameters for each region independently; in contrast, NBR estimates only the shape parameter independently for each window and uses a single scale parameter for all windows; and (3) SPG's CNN data reduction enables non-linear mapping of spatial covariate information to mutation rate, whereas NBR can perform only linear inference and disregards the spatial organization of the genome.

SPG is highly efficient for multi-resolution search, as the initial training of parameters using the CNN+GP method is the only training required; projection to each additional scale is then performed in a computationally-efficient manner. In contrast, training time for BR and NBR increases considerably as the resolution decreases. For example, performing a search across resolutions of 50 bp, 100 bp, 500 bp, 1 kb and 10 kb would require >5 hours for negative binomial, >2 hours for BR, but only several minutes for SPG.

Performing a Genome-Wide Search for Cancer Driver Mutations

For each cancer, the background mutation rate parameters were estimated across the genome using 5-fold cross validation in 10 kb, 25 kb and 50 kb regions. To search for drivers, the probabilistic model described above was applied to estimate the mutation count distributions in 50 pb regions across the genome, and then a search was performed for 50 bp regions with significantly more observed mutations than expected under the null distribution of the model. A benchmark run at 10 kb scale with 10 GP reruns takes 1-2 hours on a single 24 Gb PU, with 8 CPU cores and 756 GB RAM. Thus, a full five (5) fold of the entire genome takes 4-5 hours. Due to the model's robustness to scale, this time may be significantly reduced without drastic loss of accuracy by using larger region scales (e.g., only 30-40 minutes for a full 5-fold at 50 Kb scale). Advantageously, and according to an aspect of this disclosure, after completing the CNN+GP training, projections to lower or higher scales via the GM require no additional training. In contrast, all existing regression models (RF, NBR, BR) require retraining for each desired scale, a requirement that becomes computationally-challenging at finer resolutions (e.g., >1.5 hours for NBR and >15 hours for RF at 100 bp).

Variant Use Cases (Domains)

As noted above, SPG provides significant advantages as applied to modeling mutation rates in cancer and to facilitate identifying (through the above-described search techniques) genomic elements that drive tumor emergence. In particular, the approach facilitates identification of both known and novel putative drivers of cancer, including in the non-coding genome, a crucial open problem in genomics.

SPG is also applicable to discrete stochastic challenges in other domains, particularly when anomaly detection is one goal. For example, cybersecurity is often interested in detecting malicious network activity that may occur over seconds, hours, or weeks. Such activity ought to appear as anomalous relative to the expected network traffic. Similar to cancer drivers, however, detecting such anomalies is confounded by the fact that expected network traffic can vary dramatically over time. Thus, detecting malicious activity requires modeling non-stationary event rates and searching for anomalous activity across multiple resolutions. SPG is highly-suited for efficient execution of this task. While the details of the parameter estimation depend on the application, the variational Gaussian process approach herein may be used including with the CNN to reduce high-dimensional matrix input to an informative feature vector.

Another use case of the above-described methodology is identifying infectious disease outbreaks. The task is to determine when a new infection hotspot is developing to implement containment measures. This task is challenging because infection rates vary by geography and by individuals (e.g., young versus elderly). SGP provides a framework to identify infection hotspots while accounting for geographic and demographic risk. In this application, regional rate parameters reflect geographic infection rates while individual people represents "positions" of the stochastic process. The task then is to identify groups of people (e.g., schools, neighborhoods, cities, etc.) with more cases than expected. Local information (e.g., medical treatment availability, number of cases, population density, etc.) then serve as predictors to infer regional infection rates, while an individual's demographics provide the clustering criteria to estimate $p_i$. This application is particularly useful for identification of hotspot outbreaks of COVID-19.

The example application use cases are not intended to be limiting, as the approach herein may be used with other collections of time- and space-varying data sets. More generally, the approach may be used in association with any discrete stochastic process modeling application.

Practical Application

As noted above, the discrete stochastic process modeling approach provides significant advantages and, in particular, by enabling computationally-efficient search and retrieval of relevant events of interest, such as cancer-specific driver mutations. Once deviations (anomalies) between the estimated and observed events of interest are identified (in this case, cancer driver mutations), the resulting information is then applied to other techniques and systems, e.g., gene panel sequencing, early tumor detection, cancer drug therapeutics and methods, and the like. For example, clinical treatment decisions for a patient with cancer are often guided by the specific mutations driving the tumor. Presently, these drivers are detected, for example, using commercial testing kits such as FoundationOneCDX offered by Foundation Medicine, Inc. Such tests, however, only include known drivers. Using the above-described methods, the current set of known drivers are expanded, enabling improved and more efficient testing, clinical staging, and clinical decision-making for cancer patients. Further, numerous cancer treatments have recently been developed that target specific driver elements. For example, Erotinib (FDA-approved in 2004 and now considered a WHO essential medicine) specifically treats tumors widen by mutated EGFR. The technologies described herein increase the number of known cancer driver elements and thus increase the number of potentially druggable targets for therapeutic development. As a specific example, when designing therapeutics, non-stationary stochastic process modeling as described herein sheds light on those parts of the genome that include driver mutations, thus enabling the modeling to act as a front-end technology solution that improves the efficiency or operation of the underlying therapeutic or other technology.

Other Enabling Technologies

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines. One or more of the processes described above are implemented as computer programs, namely, as a set of computer instructions, for performing the functionality described.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system. A machine implementing the techniques herein comprises a hardware processor, and non-transitory computer memory holding computer program instructions that are executed by the processor to perform the above-described methods. Other computing systems for use herein include GPUs.

While given components of the system have been described separately, one of ordinary skill will appreciate that some of the functions may be combined or shared in given instructions, program sequences, code portions, and the like. Any application or functionality described herein may be implemented as native code, by providing hooks into another application, by facilitating use of the mechanism as a plug-in, by linking to the mechanism, and the like.

The platform functionality may be co-located or various parts/components may be separately and run as distinct functions, perhaps in one or more locations (over a distributed network).

Each above-described process preferably is implemented in computer software as a set of program instructions executable in one or more processors, as a special-purpose machine.

The techniques herein generally provide for the above-described improvements to a technology or technical field, as well as the specific technological improvements to various fields including, all as described above.

What is claimed is as follows:

1. A method of information search and retrieval associated with a non-stationary discrete stochastic process representing a pattern of mutations across a genome of a cancer of interest, wherein events of interest are cancer-specific mutations that occur within the process approximately independently at units i within a region R, and with an unknown rate $\lambda_R$ that is approximately constant across R, wherein $\lambda_R$ has an associated estimation uncertainty defined by a set of parameters that include expectation $\mu_R$ and variance $\sigma_R^2$, and wherein the non-stationary discrete stochastic process comprising a plurality of regions, wherein at least one region is a non-coding region of the genome, comprising:

responsive to a set of input data having a first dimensionality, training a model for the cancer of interest a single time to predict rate parameters and their associated estimation uncertainty for each region of the plurality of regions, the model being trained by:
processing the input data through a first process that maps patterns in the input data to a reduced data set having a second dimensionality that is at least an order of magnitude less than the first dimensionality, and
processing the reduced set through a second process to output a distribution of the events of interest and their associated estimation uncertainty for each region of the plurality of regions;
receiving a query associated with any arbitrary set of indexed positions within the plurality of regions;
responsive to receipt of the query, and by scaling existing predictions of the rate parameters and their associated estimation uncertainties from the trained model for any region of the plurality of regions, obtaining a response to the query, the response being a distribution of the events of interest and their associated estimation uncertainties for the set of indexed positions; and
providing the response for use in a target application.

2. The method as described in claim 1 wherein the query is processed using a function computed in constant time, wherein the function represents a closed form solution to a marginalization of a multi-variate probability distribution for the set of indexed positions.

3. The method as described in claim 2 wherein the closed form solution to the marginalization of the multi-variate probability distribution is a variant of a Poisson-Gamma (PG) distribution.

4. The method as described in claim 1 wherein the first process is a Convolutional Neural Network (CNN), and the second process is a Gaussian Process (GP).

5. The method as described in claim 1 wherein the first process is one of: a Convolutional Neural Network (CNN), an Auto-Encoder (AE), Principal Component Analysis (PCA), and Uniform Manifold Approximation and Projection (UMAP) learning.

6. The method as described in claim 1 wherein the second process is one of: a Gaussian Process, a Random Forest (RF) regression, a Negative Binomial Regression (NBR); and a Binomial Regression (BR).

7. The method as described in claim 1 wherein the input data is a set of genomic feature data.

8. The method as described in claim 7 wherein patterns in the input data comprise epigenetic tracks.

9. The method as described in claim 8 wherein an epigenetic track comprises a chromatin track that measures an abundance of a particular chromatin mark genome-wide.

10. The method as described in claim 4 wherein the CNN generates the reduced data set by performing a non-linear feature space reduction over information in the local epigenetic patterns.

11. The method as described in claim 1 wherein estimating the distribution of events includes formulating a closed-form generative model for a number of events of interest at any position within a particular region.

12. The method as described in claim 11 wherein the closed-form generative model is formulated using predicted regional rate parameters and their associated estimation uncertainty, together with local context information.

13. The method as described in claim 12 wherein the local context information is an observed genetic context of the particular region.

14. An information search and retrieval apparatus for use with an input dataset that is a non-stationary discrete stochastic process representing a pattern of mutations across a genome of a cancer of interest, wherein events of interest are cancer-specific mutations that occur within the process approximately independently at units i within a region R, and with an unknown rate $\lambda_R$ that is approximately constant across R, wherein $\lambda_R$ has an associated estimation uncertainty defined by a set of parameters that include expectation $\mu_R$ and variance $\sigma_R^2$, and wherein the non-stationary discrete stochastic process comprising a plurality of regions, wherein at least one region is a non-coding region of the genome, comprising:
- a hardware processor; and
- computer memory holding computer program code executed by the hardware processor, the computer program code comprising:
  - a neural network that uses the input dataset to one-time train a model for the cancer of interest to predict rate parameters and their associated estimation uncertainty for each region of the plurality of regions; and
  - a query function that receives a query associated with any arbitrary set of indexed positions within the plurality of regions and, in response, scales existing predictions of the rate parameters and their associated estimation uncertainties from the trained model for any region of the plurality of regions to obtain a response to the query, the response being a distribution of the events of interest and their associated estimation uncertainties for the set of indexed positions; and
  - an output function that applies data derived from the response to a target application.

15. A computer program product in a non-transitory computer readable medium for use in a data processing system, the computer program product holding computer program instructions which, when executed by the data processing system, are operative to perform information search and retrieval with respect to a non-stationary discrete stochastic process representing a pattern of mutations across a genome for a cancer of interest, wherein events of interest are cancer-specific mutations that occur within the process approximately independently at units i within a region R, and with an unknown rate $\lambda_R$ that is approximately constant across R, wherein $\lambda_R$ has an associated estimation uncertainty defined by a set of parameters that include expectation $\mu_R$ and variance $\sigma_R^2$, and wherein the non-stationary discrete stochastic process comprises a plurality of regions, wherein at least one region is a non-coding region of the genome, the computer program instructions comprising program code configured to:
- train a model for the cancer of interest a single time to predict rate parameters and their associated estimation uncertainty for each region of the plurality of regions;
- receiving a set of one or more queries, wherein a query is associated with any arbitrary set of indexed positions within the plurality of regions;
- responsive to receipt of each query, scale existing predictions of the rate parameters and their associated estimation uncertainties from the trained model for any region of the plurality of regions to obtain a response to the query, the response being a distribution of the events of interest and their associated estimation uncertainties for the set of indexed positions; and
- provide the response for use in a target application.

16. The computer program product as described in claim 15 wherein the program code configured to train the model comprises a neural network and a Gaussian process.

* * * * *